United States Patent

Chu et al.

[11] Patent Number: 5,610,073
[45] Date of Patent: Mar. 11, 1997

[54] USE OF CO$_2$ ABSORBANT FOR STABILIZATION OF DRIED ALKALINE REAGENT IN CREATININE ASSAY

[75] Inventors: Amy H. Chu; Wei-Sen Chu; Howard A. Cooper, all of Elkhart, Ind.

[73] Assignee: Bayer Corporation, Elkhart, Ind.

[21] Appl. No.: 534,267

[22] Filed: Sep. 26, 1995

[51] Int. Cl.$^6$ ............................................. G01N 33/00
[52] U.S. Cl. .............................. 436/98; 436/167; 436/169; 436/175; 436/176; 436/178; 422/56; 422/58; 422/69; 422/88
[58] Field of Search ................ 436/98, 164, 165, 436/167, 169, 170, 175, 176, 177, 178; 422/55, 56, 57, 58, 69, 83, 88

[56] References Cited

U.S. PATENT DOCUMENTS

| | | | |
|---|---|---|---|
| 3,800,516 | 4/1974 | Paluch | 96/150 |
| 5,203,327 | 4/1993 | Schoendorfer et al. | 128/632 |
| 5,374,561 | 12/1994 | Pugia | 436/98 |
| 5,385,847 | 1/1995 | Yip et al. | 436/534 |
| 5,464,777 | 11/1995 | Yip | 436/98 |

FOREIGN PATENT DOCUMENTS 546390  6/1993  European Pat. Off.

OTHER PUBLICATIONS

Patent Abstracts of Japan, Sasaki et al., JP Application No. 62–287261, published Aug. 21, 1989.

*Primary Examiner*—Jill Warden
*Assistant Examiner*—Maureen M. Wallenhorst
*Attorney, Agent, or Firm*—Jerome L. Jeffers

[57] ABSTRACT

Disclosed is an improvement to the method for the detection of creatinine in which creatinine, in aqueous solution, is contacted with a dry reagent system of an indicator for creatinine. The assay is carried out at a pH above about 11.5 which is maintained by an alkaline material. The improvement involves packaging the reagent system with a material capable of absorbing CO$_2$ and at least some ambient water vapor. This inhibits the formation of carbonic acid thereby reducing the neutralization of the alkaline reagent system during storage to increase the shelf life and decrease the variability of the system.

12 Claims, 4 Drawing Sheets

USE OF CO₂ ABSORBANT FOR STABILIZATION OF DRIED ALKALINE REAGENT IN CREATININE ASSAY

BACKGROUND OF THE INVENTION

Creatinine is the end metabolite when creatine becomes creatine phosphate and is used as an energy source for muscle contraction. The creatinine produced is filtered by the kidney glomeruli and then excreted into the urine without reabsorption. The determination of creatinine in body fluids is useful for diagnosing muscle diseases or various kidney diseases such as nephritis and renal insufficiency.

The first practical test for the determination of creatinine in urine or serum, known as the Jaffe method, involves the formation of the red-yellowish brown colored creatinine picrate by the bonding of picric acid and creatinine in an alkaline solution. A more recent method for creatinine determination is reported by Benedict and Behre in *J. Biol. Chem.*, 113:515 (1936) which involves the reaction of 3,5-dinitrobenzoic acid DNBA with creatinine in an alkaline medium. Each of these reactions require a high pH, i.e. greater than about 11.5 and typically from about 12 to about 14, in order to deprotonate the creatinine in order for the system to operate properly. Strongly basic substances such as alkali and alkaline earth metal hydroxides are typically used to maintain a suitably high pH in these reagent systems.

The dried creatinine reagent system comprising an indicator which forms a colored reaction product at an elevated pH and an alkaline reagent to raise the pH to the desired level when the reagent is rehydrolyzed can be applied to an absorbant carrier such as filter paper or a porous film. Typically, the reagent system is applied to the carrier in the form of separate solutions, aqueous for the alkali and organic for the indicator, with evaporation of the solvent to leave the residual dry reagent dispersed in the carrier. This sort of system is disclosed in Japanese Patent Application No. 62-287261 which also discloses treating the strip with an alkali soluble carboxylic acid derivative polymer to inhibit degradation of the strip by the strong alkali.

There are available diagnostic devices for the determination of protein, particularly human serum albumin (HSA), in urine. The determination of HSA in urine has clinical significance for the detection of the early stages of nephropathy which is an abnormal state of the kidney. A high percentage of individuals suffering from insulin dependent diabetes mellitus (IDDM) and noninsulin dependent diabetes mellitus (NIDDM) eventually secrete HSA at levels above those of the upper end of the normal population. This stage of "microalbuminuria" becomes progressively worse and typically leads to nephropathy. Since the kidney damage at the stage of microalbuminuria can be controlled or reversed by administering appropriate therapy, it is well recognized that measuring microalbuminuria is part of the comprehensive care of IDDM and NIDDM.

Other urine bound proteins, e.g. IgG, alpha-1-microglobulin, Bence-Jones protein and N-acetyl-b-D-glucoseaminidase, are useful as markers to detect and differentiate prerenal, glomeruler and postrenal forms of microalbuminuria. Proteinuria, which is indicated if the protein concentration in urine is greater than 30 mg/L, is the common symptom for a variety of different kidney diseases. Accordingly, there is a need on the part of nephrologists, diabetologists and cardiologists for test methods that are sensitive, specific and quantitative for the determination of these proteins in urine.

In order to increase the sensitivity and specificity of urinary protein assays and minimize the problem of high urine flow rate resulting in urine dilution, protein/creatinine ratios are used in urine protein assay results to normalize the urine concentration. Typical protein analyses involve immunoassays such as radioimmunoassay, enzyme immunoassay, latex assisted immunoassay and immunoturbidimetric assay. Since the commonly used Jaffe and Benedict-Behre creatinine assays are run at a high pH, the common practice in clinical laboratories is to run the protein and creatinine assays separately and then combine the values obtained from these assays to generate the protein to creatinine ratio. Since patients with high urine flow rates tend to have artificially low protein values due to the urine's dilution and since creatinine is a good marker for dilution of urine, the use of the protein/creatinine ratio eliminates the problem of urine dilution and gives a more accurate reflection of the true protein excretion rate.

In U.S. Pat. 5,385,847 there is disclosed a device which permits the determination of protein and creatinine in a single urine sample in a reaction vessel in which there is carried out an immuno assay for the protein in the vessel's first reaction zone followed by the creatinine determination in a second reaction zone which contains a dried indicator for the determination of creatinine as well as the dried basic reagent which is necessary for raising the pH of the reaction medium when the reagents are rehydrated by introduction of the liquid sample to be tested into the second reaction zone.

Whether the dry creatinine reagent (indicator and alkaline material) be in the strip form or located in the device of the '847 patent, whose disclosure is incorporated herein by reference, there exists a storage problem due to the formation of carbonic acid from atmospheric moisture and carbon dioxide in the area of the dried alkali which, over time, can cause its neutralization thereby limiting or destroying its ability to induce the high pH necessary for the determination of creatinine in the test fluid. Typically, these devices have been packaged with a desiccant to reduce moisture in the system to thereby inhibit the formation of carbonic acid. Examples of such desiccants include molecular sieves, silica gel, sodium sulfate, magnesium chloride, lithium chloride and triethylene glycol. The use of a desiccant which serves merely as a drying agent has not proved entirely satisfactory which observation caused us to search for a more satisfactory class of desiccant.

Soda lime, a mixture of sodium hydroxide and calcium oxide, is described in Hackh's Chemical Dictionary, 4$^{th}$ Edition, as a general absorbant for acid gases. In Kirkothmer, Encyclopedia of Chemical Technology, 3$^{rd}$ Edition, there is described on pages 674–678 of Volume 16 a sodium chlorate based generator for the production of oxygen. The generator comes equipped with a filter system which includes soda lime for the removal of byproduct $CO^2$ from the oxygen stream.

SUMMARY OF THE INVENTION

The present invention relates to a method for the detection of creatinine in which an aqueous solution containing creatinine is contacted with a dry reagent system containing an indicator for creatinine at a pH above about 11.5. The high pH is provided by a dry alkaline material upon its being hydrated by the aqueous fluid. The present invention involves an improvement to the creatinine detection system which involves packaging the dry reagent with a material capable of absorbing $CO_2$ and at least some ambient water vapor. The $CO_2$ absorbing material is provided in an amount sufficient to substantially inhibit the formation of carbonic acid in the area of the reagent system. This inhibition of the production of carbonic acid increases the shelf life of the creatinine detecting device by reducing or eliminating the neutralization of the alkali reagent by carbonic acid formed in situ.

Also included within the scope of the invention is a packaged creatinine detecting device containing the $CO_2$ absorbing material.

DESCRIPTION OF THE INVENTION

Figure 1:
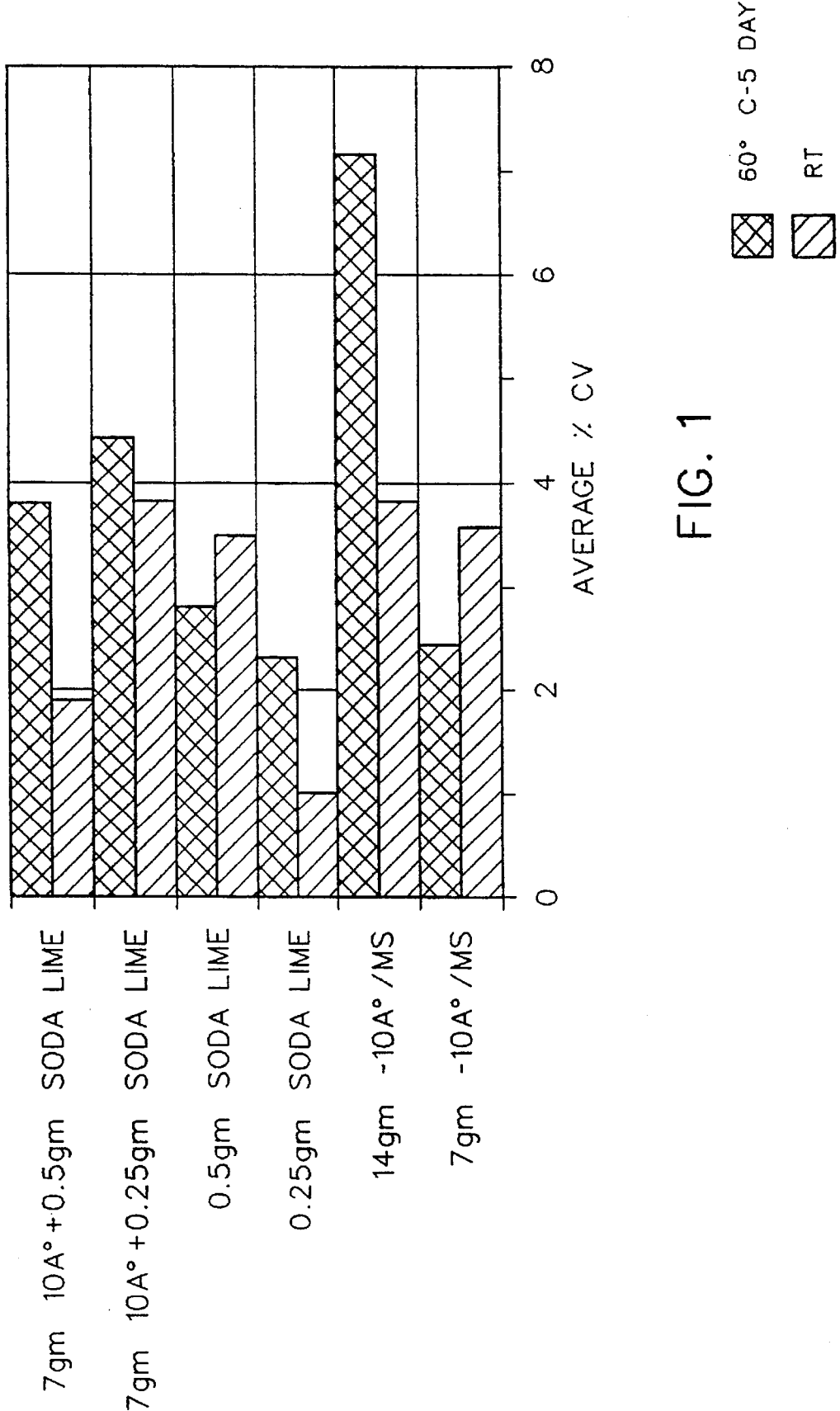
FIG. 1 shows, in graphical form, the consistence of performance obtained using soda lime and a combination of soda lime with a molecular sieve.

Suitable $CO_2$ absorbing materials for use in the present invention include soda lime, Ascarite® (sodium hydroxide coated silicate), lithium hydroxide, barium hydroxide, calcium hydroxide and potassium hydroxide. While the present invention is not predicated upon any mechanism of action, it is believed that these $CO_2$ "scavengers" extend the useful life of the creatinine reagent by competing with the alkali contained therein for atmospheric $CO_2$. This inhibits neutralization of the alkali by diverting $CO_2$ and water vapor from the creatinine alkaline reagent to the $CO_2$ scavenger thereby preventing the absorbtion of the $CO_2$ and water vapor by the creatinine reagent as represented by the following mechanism:

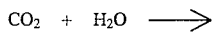

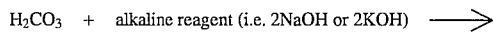

or

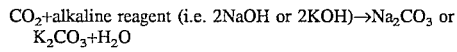

Either of these two possibilities will result in loss of alkalinity by consuming the NaOH or KOH of the creatinine alkaline reagent.

Conversely, in the case of a desiccant such as soda lime which is also capable of scavenging $CO_2$, the following reactions will occur:

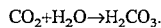  1.

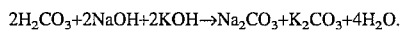  2.

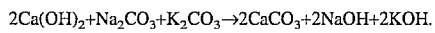  3.

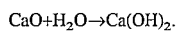  4.

The $CO_2$ first reacts with water to form carbonic acid and subsequently reacts with the hydroxides to form soluble salts of both sodium and potassium carbonate. The soluble salts then react with the calcium hydroxide to form insoluble calcium carbonate. The rapidity of CO removal is directly proportional to the rate of generating active hydroxide from reaction 3 and reaction 4. Therefore, the $CO_2$ absorbing material should also absorb water vapor (reaction 1 and reaction 4).

The system containing the dry creatinine reagent, whether it be in the form of a test strip or the previously described cartridge device for determining protein and creatinine in a single test vessel, will normally be packaged in an aluminum foil pouch for the test cartridge or a polypropylene bottle for the test strip to exclude atmospheric gases and water vapor. However, as a practical matter, the packaging materials do not form a perfect seal and do allow some atmospheric gases such as $CO_2$ and water vapor to enter the package over time. The prior use of pure desiccants to absorb moisture which enters the package has not been totally successful because a desiccant such as silica gel or a 3 Å, 4 Å or 10 Å molecular sieve is more effective in absorbing water vapor and cannot prevent the interaction between the alkaline reagent and $CO_2$ which causes neutralization of the alkaline reagent. Although a 10 Å molecular sieve can also absorb $CO_2$, the binding between $CO_2$ and the molecular sieve is weak and reversible. This is in sharp contrast to soda lime which absorbs $CO_2$ and water vapor thereby converting them irreversibly into calcium carbonate. We have found that the use of materials which absorb $CO_2$ are more suitable for extending the shelf life of packaged diagnostic devices for the determination of creatinine than are pure $H_2O$ desiccants. It is also desirable that the $CO_2$ absorbant have some desiccant capability of its own due to the hygroscopic nature of the alkaline reagent. Alternatively, a separate desiccant can be included in the package along with the $CO_2$ absorbant although most materials which are capable of absorbing CO are also sufficiently hygroscopic in themselves to eliminate the need for a separate desiccant. It is not desirable to over desiccate the reagent containing device. This can be determined from FIG. 1 whose data indicate that greater consistency of performance was obtained with soda lime than with the combination of soda lime and molecular sieve. The possible reasons why the combination of $CO_2$ absorbant (in this case soda lime) and the molecular sieve did not work as well as the soda lime by itself are:

1) the molecular sieve (4 Å or 10 Å) can also absorb $CO_2$ reversibly but with a lesser absorbing capacity than soda lime or the creatinine alkaline reagent. Accordingly, the $CO_2$ absorbed by the molecular sieve may "pass on" to the alkaline reagent resulting in the decreasing alkalinity of the creatine alkaline reagent.

2) the $CO_2$ absorbing capacity of soda lime is increased by its increasing moisture content. Over desiccation (i.e. a combination of the molecular sieve and soda lime) which decreases the soda lime's moisture content may, therefore, also decrease its $CO_2$ absorbing capacity.

In practicing the present invention, the creatinine detecting device is packaged with the $CO_2$ moisture absorbant in a gas and moisture barrier container. The amount of absorbant is not critical since any amount will tend to increase the shelf life of the device. Typically, the $CO_2$ absorbant will comprise from about 25 to 200% of the alkaline material on a weight/weight basis.

Of course the optional amount of $CO_2$ absorbant will depend on the size of the package in which the creatinine reagent is stored. If the package is totally impermeable to $CO_2$ and moisture only enough $CO_2$ absorbant to remove residual amounts of these materials will be required. As a practical matter, one would expect the package to permit some finite leakage of ambient gases thereby requiring the use of greater amounts of the $CO_2$ absorbant to ensure that the creatinine reagent is well protected through its intended shelf life. Experimental results indicate that acceptable creatinine alkaline reagent shelf life with as little as 0.1 gm and as high as 4 gm of $CO_2$ absorbant present in the reagent package containing 30 mg of the alkaline reagent. Due to the hygroscopic nature of the dried creatinine alkaline reagent, it can readily absorb moisture from the $CO_2$ absorbant resulting in a detrimental effect on the performance of the alkaline reagent. This phenomena renders the initial moisture content of the $CO_2$ absorbant very important and limits the permissible amount of moisture in the $CO_2$ absorbant to a maximum of about 4% (w/w) of the $CO_2$ absorbant.

The method of practicing the present invention and the advantages realized thereby are further illustrated by the following examples:

EXAMPLE I

Effect of Soda Lime on Creatinine Dried Reagent Performance.

Cartridges suitable for the detection of creatinine are prepared as follows:

The alkaline reagent for creatinine comprises either an alkali hydroxide solution or a mixture of buffering material such as phosphate, borate or guanidine derivatives with an alkali hydroxide. Typically, a mixture of 1M potassium phosphate and 2.5M potassium hydroxide was prepared. The mixture also contains an additive, e.g. a monosaccharide, disaccharide or oligosaccharide, for drying down the alkaline reagent on the mesa of the polyacrylic cartridge. A volume of 15 µL of reagent is deposited and dried onto the mesa using a drying tunnel (temperature 60° C.) and air flow rates set at 75% of the maximum for 15 minutes.

The DNBA reagent is either dried down on the mesa of the cartridge or contained in the buffer tray of the test device. The formulation of the dried DNBA reagent contains 1.4M DNBA dissolved in 2.5M Li OH with 2.5% water soluble polyvinyl alcohol added to dry down the reagent. Alternatively, the DNBA can be dissolved with buffer at a pH range of 6 to 9.

The test cartridge may contain other dried reagents such as human serum albumin and antibody for the determination of urinary albumin as disclosed in U.S. Pat. No. 5,385,847 so that the ratio of the analyte to creatinine can be obtained to normalize the test result.

The test cartridges are placed in a sealed aluminum foil pouch containing a soda lime packet, i.e. soda lime in a TYVEK® fiber pouch as desiccant.

Included in each of the packages, were either soda lime (0.25 or 0.5 gm per packet), 10 Å molecular sieve from Multiform Desiccants Inc. (one 7 gm packet or two 7 gm packets per cartridge). The soda lime used was Sodasorb® from W. R. Grace & Company. Cartridges were also packaged with the combination of either 0.25 gm or 0.5 gm of soda lime and a single 7 gm packet of the 10 Å molecular sieve. Replicates of 5 each of the cartridges were stored either at room temperature or 60° C. for 5 days at ambient humidity. The performance of the cartridges was evaluated with aqueous creatinine calibrators (containing 150 or 500 mg/dL creatinine) with the absorbance at 105 seconds being used to calculate the reactivity of the cartridge. Based on a predetermined calibration curve for each lot of cartridges, the absorbance was converted into clinical units of creatinine using a converting algorithm. The mean and standard deviation of the five replicates were calculated and the coefficient of variation (% CV) was determined by dividing the standard deviation by the mean times 100.

The coefficients of variation are graphically presented in FIG. 1. From FIG. 1 it can be determined that comparing the precision (expressed as % CV of the reagent) with different amounts of molecular sieve, soda lime, or combination of molecular sieve with soda lime, the % CV was improved by using as little as 0.25 gm of soda lime. Increasing the amount of molecular sieve from 7 gm to 14 gm worsens the precision of the creatinine reagent. Doubling the soda lime concentration or combining soda lime with molecular sieve did not improve the precision of the reagent.

Figure 2:
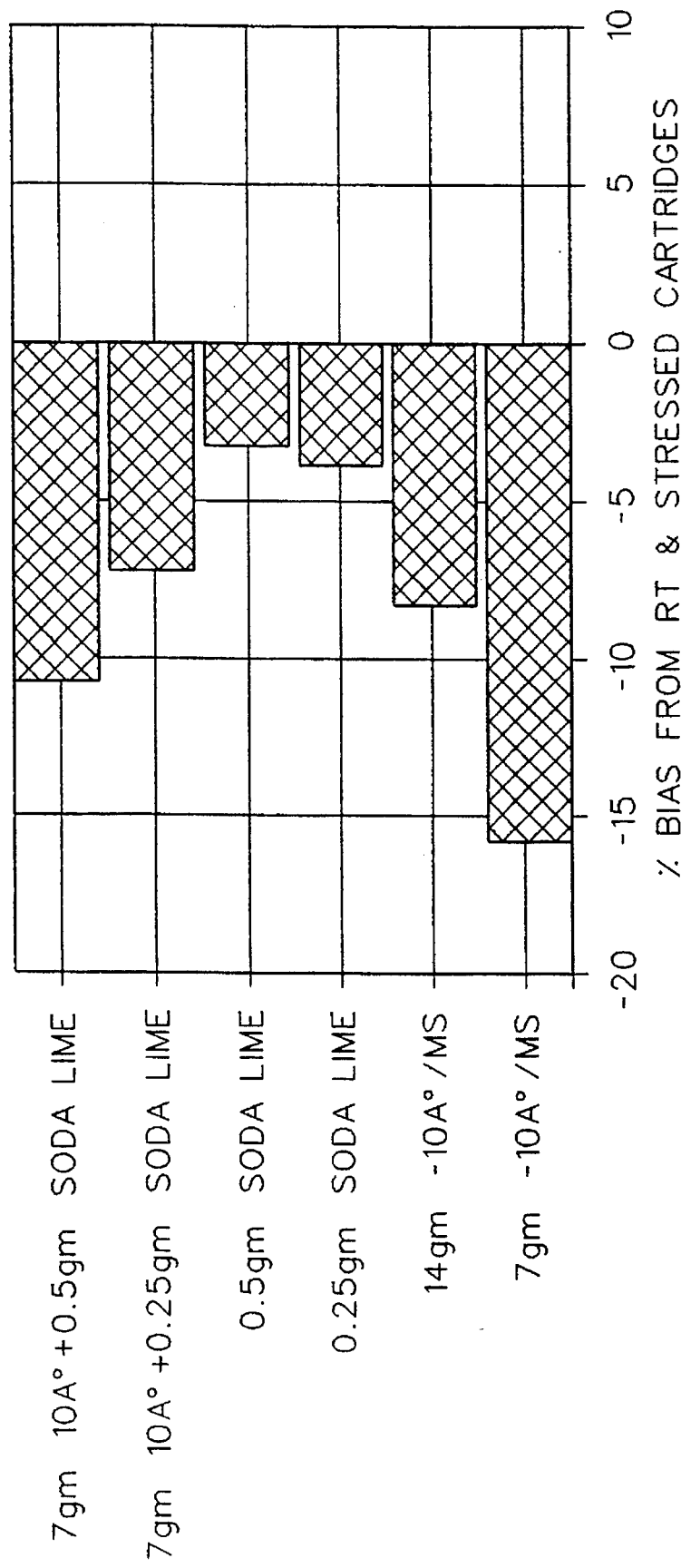
FIG. 2 is a graph showing the difference between room temperature and 60° C. obtained when cartridges packed with different types of desiccant were stored for 5 days.

To assess the stability of the creatinine alkaline reagent, the reagent cartridges were stored at room temperature or stressed at 60° C. for 5 days. Both the room temperature and the stressed cartridges were evaluated with samples containing 150 mg/dL and 500 mg/dL of creatinine. Five replicates per sample were run on 5 DCA 2000® hemglobin analyzer instruments from Bayer Diagnostics. The absorbance at 105 seconds was used to calculate the reactivity of each cartridge. Based on a pre-determined calibration curve for each lot of cartridges, the absorbance was converted into clinical units of creatinine using a converting algorithm. The mean clinical unit of the five replicates for each sample was calculated. The difference in mean clinical units between room temperature and 60° C. for the five days stressed cartridges which were packaged with different types of desiccant is illustrated by FIG. 2. The results indicate that the reagent cartridges packaged with soda lime desiccant showed the least bias between room temperature and 60° C. stressed cartridges, indicating that the reagent is more stable with soda lime as the desiccant. Conversely, a large stability bias was observed for reagent cartridges packaged with molecular sieve. Combining molecular sieve with soda lime resulted in greater bias than with soda lime alone.

Example II

Cartridges of the type described above were packaged with soda lime (0.1 gm/packet, 0.2 gm/packet or 1 gm/packet), molecular sieve (2 gm of 4 Å or 7 gm of 10 Å), 2 gm silica gel or a combination of molecular sieve and soda lime. The cartridges were either stored at room temperature or at 60° C. for 5 days. The performance of the cartridges was evaluated with two levels of creatinine calibrator at 150 and 500 mg/dL creatinine (FIG. 3) or three levels of creatinine calibrator at 30, 150 and 500 mg/dL creatinine (FIG. 4). Each of the 5 replicates were evaluated for creatinine concentration whereupon the % bias between room temperature and stressed cartridges was calculated from the mean clinical values obtained. The average % bias for creatinine reagents packaged with different types of desiccant were evaluated with 150 and 500 mg/dL samples are set out graphically in FIG. 3.

Figure 3:
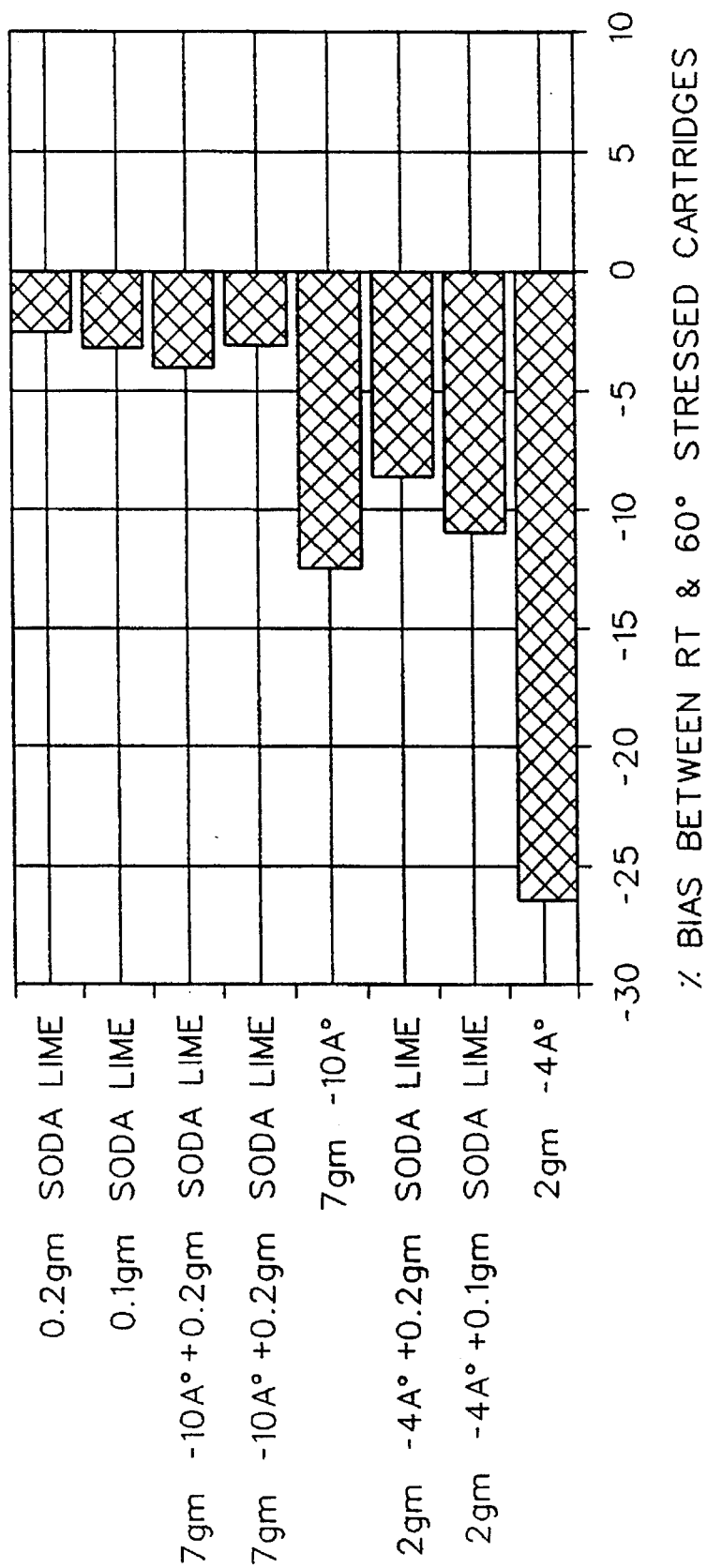
FIG. 3 sets out graphically the average bias for creatinine reagents packaged with different types of reagent.
Figure 4:
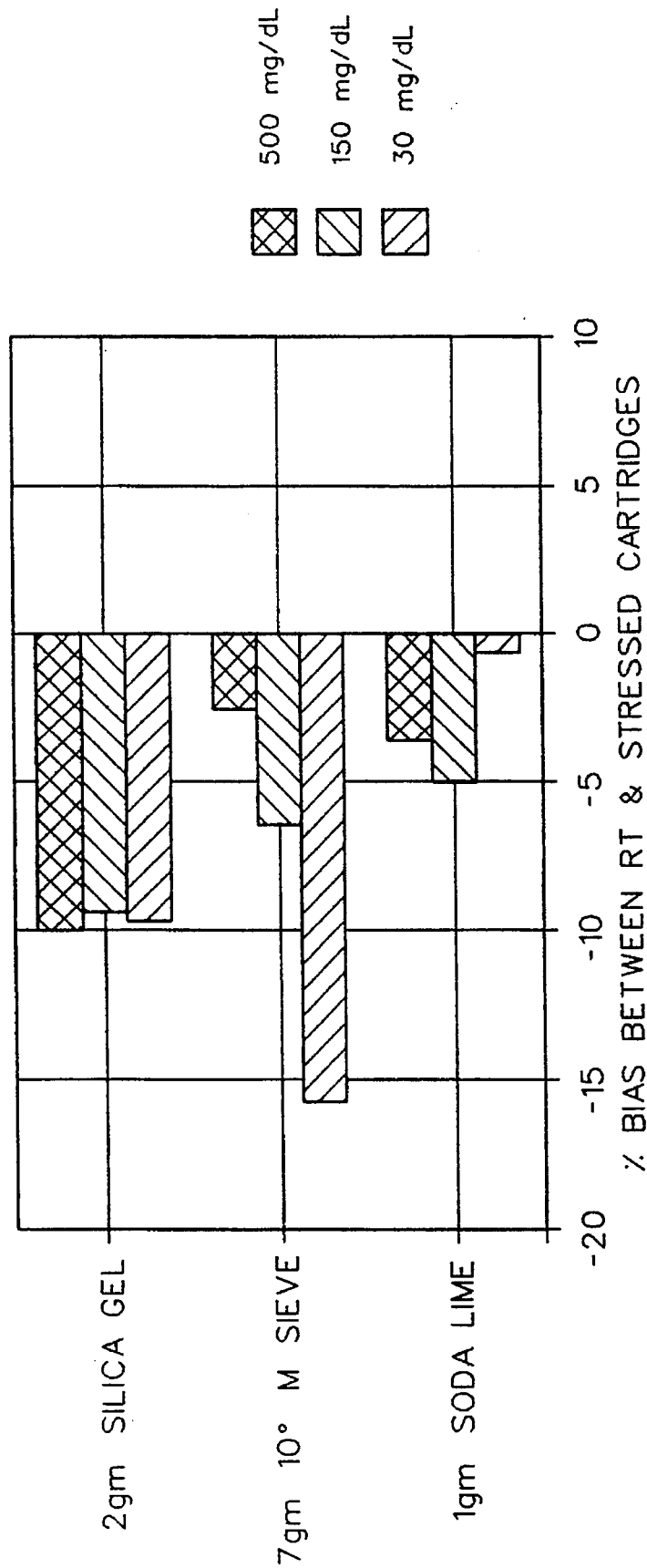
FIG. 4 shows the average bias for creatinine reagents using 3 separate calibrators.

FIG. 3 shows that the reagent cartridges packaged with 2 gm of 4 Å molecular sieve showed the worst stability bias. The bias was decreased from −25% to −13% by changing the desiccant to 7 gm of 10 Å molecular sieve. The smallest bias (less than 5%) was obtained for the reagent cartridges packaged with as little as 0.1 gm soda lime. The combination of 7 gm of 10 Å molecular sieve with soda lime did not offer any advantage. From these data, one can conclude that soda lime is the best desiccant for stabilizing the reagent cartridge.

The results from FIG. 4, which shows the bias for individual samples, demonstrate that the reagent cartridges packaged with soda lime show the smallest stability bias for all three levels of creatinine calibrator when compared with cartridges packaged with silica gel or 7 gm of 10 Å molecular sieve.

What is claimed is:

1. In a method for the detection of creatinine in which creatinine in aqueous solution is contacted with a dry reagent system comprising an indicator for creatinine at a pH above about 11.5 which pH is maintained by an alkaline material, the improvement which comprises packaging the reagent system with a material capable of absorbing $CO_2$ and at least some ambient water vapor in sufficient amount to substantially inhibit the formation of carbonic acid in the area of the reagent system to thereby reduce the neutralization of the alkaline material during storage.

2. The method of claim 1 wherein the alkaline material is capable of maintaining the pH of the reagent system at a level of from about 12 to 14.

3. The method of claim 1 wherein the dry reagent system for detecting creatinine is carried by an absorbant carrier in the form of a test strip.

4. The method of claim 1 wherein the dry reagent system is contained in a reaction vessel which contains a first reaction zone in which is carried out an immunoassay for a protein in a urine test sample and a second reaction zone which contains the dry reagent system.

5. The method of claim 1 wherein the $CO_2$ absorbing material is selected from the group consisting of soda lime, sodium hydroxide coated silicate, lithium hydroxide, barium hydroxide, calcium hydroxide and potassium hydroxide.

6. The method of claim 5 wherein the $CO_2$ absorbing material is soda lime.

7. The method of claim 1 wherein the $CO_2$ absorbing material is present in an amount of from about 25 to about 200% (w/w) of the alkaline material.

8. The method of claim 1 wherein the indicator for creatine is 3,5-dinitrobenzoic acid and the alkaline material is sodium hydroxide.

9. A device for the detection of creatinine in an aqueous solution which device comprises a reagent system comprising an indicator for creatinine which indicator operates at a pH of above about 11.5 and an alkaline material, wherein the device is packaged with a material capable of absorbing $CO_2$ and water vapor and wherein the material capable of absorbing $CO_2$ is present in an amount sufficient to substantially inhibit the formation of carbonic acid in the area of the reagent system.

10. The device of claim 9 which is in the form of an absorbant carrier in which the reagent system for the detection of creatinine is contained.

11. The device of claim 9 which is in the form of a reaction vessel which contains a first reaction zone for carrying out an immunoassay and a second reagent zone containing the reagent system.

12. The device of claim 9 wherein the $CO_2$ absorbing material is soda lime.

* * * * *